US006572750B1

(12) United States Patent
Cong et al.

(10) Patent No.: US 6,572,750 B1
(45) Date of Patent: Jun. 3, 2003

(54) HYDRODYNAMIC INJECTOR (75) Inventors: Peijun Cong, San Jose, CA (US); Robert D. Doolen, Sunnyvale, CA (US); Tony N. Wheeler, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 135 days.

(21) Appl. No.: 09/620,987

(22) Filed: Jul. 21, 2000

(51) Int. Cl.[7] .................... G01N 27/447; G01N 27/453
(52) U.S. Cl. ................... 204/453; 204/601; 204/604; 204/451
(58) Field of Search ................... 204/451, 453, 204/601, 604

(56) References Cited

U.S. PATENT DOCUMENTS

| | | | |
|---|---|---|---|
| 3,655,980 A | 4/1972 | Bossen | 250/82.3 D |
| 4,172,227 A | 10/1979 | Tyrer et al. | 250/461 B |
| 4,375,163 A | 3/1983 | Yang | 763/61.1 C |
| 4,576,477 A | 3/1986 | Corbet et al. | 356/39 |
| 4,618,769 A | 10/1986 | Johnson et al. | 250/338 |
| 4,747,686 A | 5/1988 | Sato | 356/72 |
| 5,003,488 A | 3/1991 | Hardy | 364/509 |
| 5,045,172 A | 9/1991 | Guzman | 204/299 R |
| 5,066,382 A | 11/1991 | Weinberger et al. | 204/299 R |
| 5,085,757 A | 2/1992 | Karger et al. | 204/299 R |
| 5,239,360 A | 8/1993 | Moring et al. | 356/344 |
| 5,274,240 A | 12/1993 | Mathies et al. | 250/458.1 |
| 5,302,264 A | * 4/1994 | Welch et al. | 204/452 |

(List continued on next page.)

FOREIGN PATENT DOCUMENTS

WO            99/42819        8/1999

OTHER PUBLICATIONS

Culbertson, C.T. et al., "Lowering The UV Absorbance Detection Limit In Capillary Zone Electrophesis Using A Single Linear Photodiode Array Detector", *Anal. Chem.*, vol. 70, pp. 2629–2638, 1998. Jul.
Gong, Xiaoyi et al., "An Absorption Detection Approach For Multiplexed Capillary Electrophoresis Using A Linear Photodiode Array", *Analytical Chemistry*, pp. A–H, 1999.
Product Catalog, "Swagelok® BMS Series Bellows Sealed Metering Valves", Nupro Company, Feb. 1997.
Product Catalog, "Swagelok® Ultra–High–Purity Diaphragm Valve; DA Series", Nupro Company, May 1998.
Product Bulletin 640/641, "Electronic Pressure Controllers, 640 Series", MKS Instruments, Inc., Jul. 1995.

*Primary Examiner*—Jill Warden
*Assistant Examiner*—Alexander Noguerola
(74) *Attorney, Agent, or Firm*—Senniger, Powers, Leavitt & Roedel (57) ABSTRACT

A hydrodynamic injector for substantially concurrently loading fluid samples to be analyzed into multiple capillary tubes of a capillary electrophoresis system. The injector includes an enclosure defining a pressure chamber for holding multiple receptacles, each containing a fluid sample, and apertures in the enclosure for passing capillary tubes into a position inside the pressure chamber and in fluid communication with the samples in respective receptacles. Electrodes on the enclosure extend into the pressure chamber for reception in the receptacles. The pressure chamber is pressurized with gas to substantially concurrently force the fluid samples from respective receptacles into the capillary tubes in preparation for a capillary electrophoresis operation.

33 Claims, 9 Drawing Sheets

U.S. PATENT DOCUMENTS

| | | | | |
|---|---|---|---|---|
| 5,303,021 A | | 4/1994 | Kita | 356/72 |
| 5,312,535 A | | 5/1994 | Wasaka et al. | 204/299 R |
| 5,324,401 A | | 6/1994 | Yeung et al. | 204/180.1 |
| 5,358,613 A | * | 10/1994 | Schneider et al. | 204/453 |
| 5,397,772 A | * | 3/1995 | Ribeiro et al. | 435/69.1 |
| 5,413,686 A | | 5/1995 | Klein et al. | 204/299 R |
| 5,439,578 A | | 8/1995 | Dovichi et al. | 204/299 R |
| 5,488,240 A | | 1/1996 | Hlousek et al. | 250/231.16 |
| 5,569,366 A | * | 10/1996 | Chen et al. | 204/451 |
| 5,582,705 A | | 12/1996 | Yeung et al. | 204/203 |
| 5,611,903 A | | 3/1997 | Janssens et al. | 204/454 |
| 5,695,626 A | | 12/1997 | Yeung et al. | 204/605 |
| 5,730,850 A | | 3/1998 | Kambara et al. | 204/603 |
| 5,741,441 A | | 4/1998 | Yeung et al. | 204/452 |
| 5,900,934 A | | 5/1999 | Gilby et al. | 356/344 |
| 6,027,627 A | * | 2/2000 | Li et al. | 204/451 |
| 6,297,009 B1 | * | 10/2001 | Demorest et al. | 204/451 |

* cited by examiner

HYDRODYNAMIC INJECTOR

BACKGROUND OF THE INVENTION

This invention is generally in the field of capillary electrophoresis, and relates particularly to apparatus and method for substantially concurrently loading fluid samples to be analyzed into multiple capillary tubes of a multiplexed or "parallel" capillary electrophoresis system.

Capillary electrophoresis (CE) is a chemical separation technique involving the use of one or more capillary tubes. Parallel CE, a recently developed technique using many parallel capillary tubes, is growing in popularity since this technology allows multiple samples to be analyzed quickly and efficiently. This is particularly advantageous in combinatorial chemistry where many hundreds and even thousands of samples are analyzed over a short period of time. Parallel CE involves the use of a "bundle" of capillary tubes, e.g., 96 such tubes. A chemical sample to be analyzed is loaded in each tube, and a high voltage is applied to the tube, causing the components of the sample to migrate in the tube at different speeds, thereby causing separation of the components which can then be analyzed by conventional light absorption or other techniques. Reference may be made to the following patents and publications for a more detailed description of CE, including parallel CE, and various analytical techniques used in CE: U.S. Pat. Nos. 5,900,934, 5,324,401, 5,312,535, 5,303,021, 5,239,360; C. Culbertson et al., *Analytical Chemistry*, 70, 2629–2638 (1998); and X. Gong et al., *Analytical Chemistry*, 71(21); 4989–4996 (1999).

In prior multiplexed CE systems, the capillary tubes have been loaded with liquid samples either hydrostatically (i.e., by siphoning) or electrokinetically. However, these methods have various drawbacks, and there is a need for an improved loading system which is more reliable, reproducible and versatile.

SUMMARY OF THE INVENTION

Among the several objects of this invention may be noted the provision of a hydrodynamic injector for loading liquid samples into the inlet ends of multiple capillary tubes in preparation for a CE operation; the provision of such an injector which loads capillary tubes substantially concurrently and very quickly using a standard microtiter plate; the provision of such an injector which is easy to operate; the provision of such an injector which can be used to flush and condition the capillary tubes prior to sample loading; the provision of such an injector which is safe to use; the provision of two such injectors which can be used at opposite ends of the capillary tubes to enable loading from both ends of the tubes; and the provision of a method of simultaneously transferring liquid samples into the inlet ends of multiple capillary tubes to carry out a CE operation.

In general, the present invention is directed to a hydrodynamic injector for substantially concurrently loading fluid samples to be analyzed into multiple capillary tubes of a capillary electrophoresis system, the tubes having first and second ends. The injector comprises an enclosure defining a pressure chamber for holding multiple receptacles, each containing a fluid sample therein, and apertures in the enclosure for passing capillary tubes into a position wherein first ends of the tubes are positioned in the pressure chamber in fluid communication with the samples in respective receptacles. Electrodes on the enclosure extend into the pressure chamber for reception in the receptacles. The enclosure has a gas inlet for pressurizing the pressure chamber whereby the fluid samples are substantially concurrently forced from respective receptacles into the first ends of respective capillary tubes in preparation for a capillary electrophoresis operation.

The present invention is also directed to a hydrodynamic injector of the type described above where the enclosure comprises a channel surrounding the pressure chamber and communicating with the gas inlet, and passages connecting the channel and the pressure chamber at spaced intervals around the pressure chamber.

In another aspect, a hydrodynamic injector of the present invention comprises second enclosure having a second pressure chamber therein containing one or more receptacles for receiving fluid samples transmitted through the capillary tubes from the first enclosure, apertures in the second enclosure for passing said capillary tubes into a position wherein second ends of the tubes are positioned in the second pressure chamber for the flow of fluid into the one or more receptacles, and electrodes on the second enclosure extending into the second pressure chamber for reception in the one or more receptacles. The second pressure chamber is adapted for holding multiple receptacles, each containing a fluid sample therein. The second enclosure has a gas inlet for pressurizing the pressure chamber whereby the fluid samples in the second enclosure are simultaneously forced from respective receptacles into the second ends of respective capillary tubes in preparation for a capillary electrophoresis operation.

A method of this invention generally involves the substantially concurrent transfer of fluid samples from multiple receptacles into first ends of multiple capillary tubes. The method comprises positioning the first ends of the capillary tubes and the receptacles in a single pressure chamber so that the first ends are in fluid communication with the samples in the receptacles, pressurizing the pressure chamber to force fluid from the receptacles into the capillary tubes, and causing an electric current to flow through the capillary tubes and contents thereof to cause a first capillary electrophoresis operation.

In another embodiment, a method of the present invention further involves an additional step of positioning second ends of the capillary tubes in a second pressure chamber containing multiple receptacles for receiving the second ends.

In still another embodiment, the pressurizing step involves pressurizing an accumulator to a predetermined pressure and, after the predetermined pressure has been reached, opening a valve to establish gas flow communication between the accumulator and the pressure chamber to pressurize the pressure chamber.

Other objects and features of this invention will be in part apparent and in part pointed out hereinafter.

BRIEF DESCRIPTION OF THE DRAWINGS

Corresponding parts are designated by corresponding reference numbers throughout the drawings.

DETAILED DESCRIPTION OF THE PREFERRED EMBODIMENT

Figure 1:
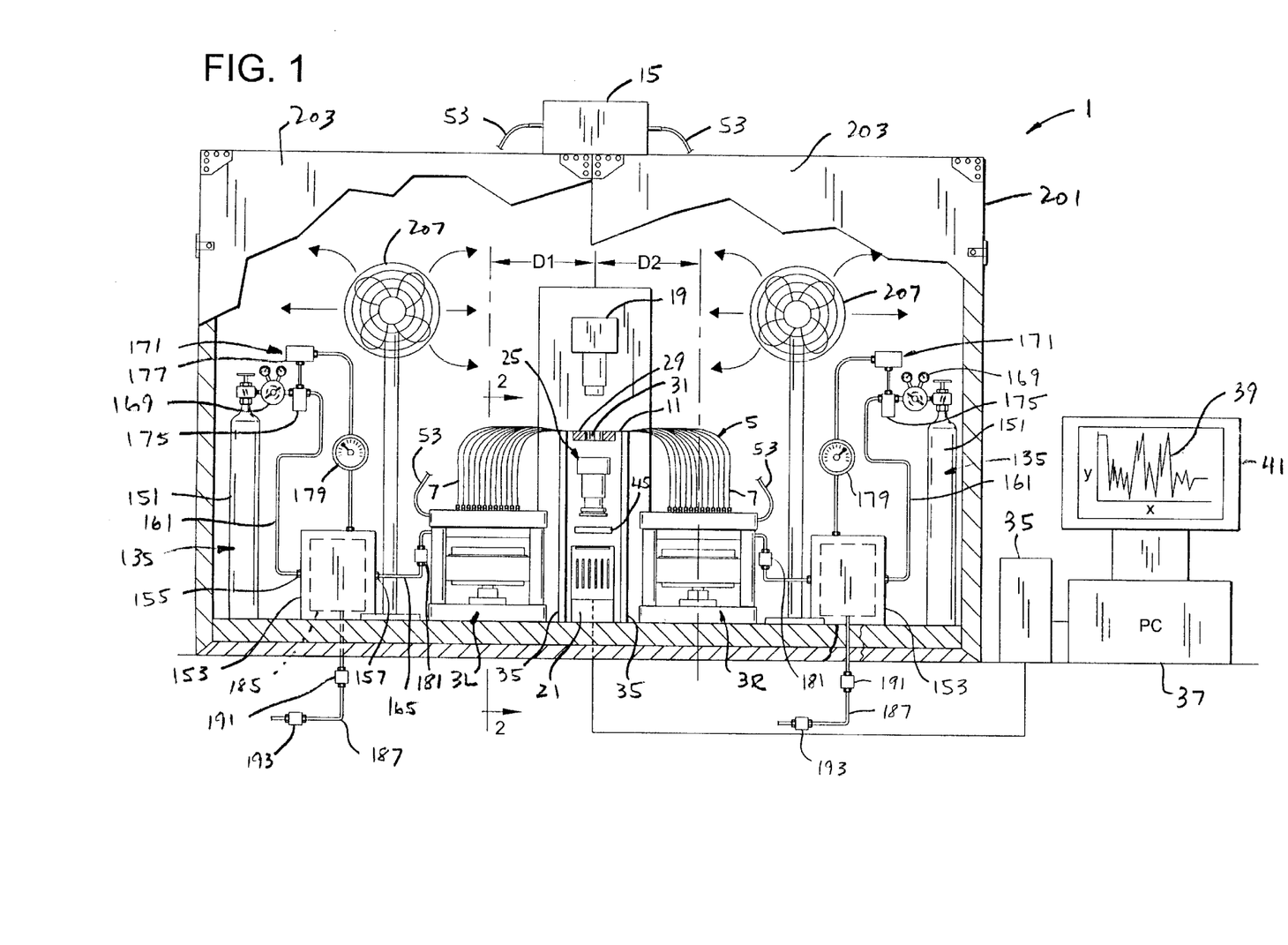
FIG. 1 is a schematic view of a parallel CE system using a pair of hydrodynamic injectors of the present invention.
Figure 1A:
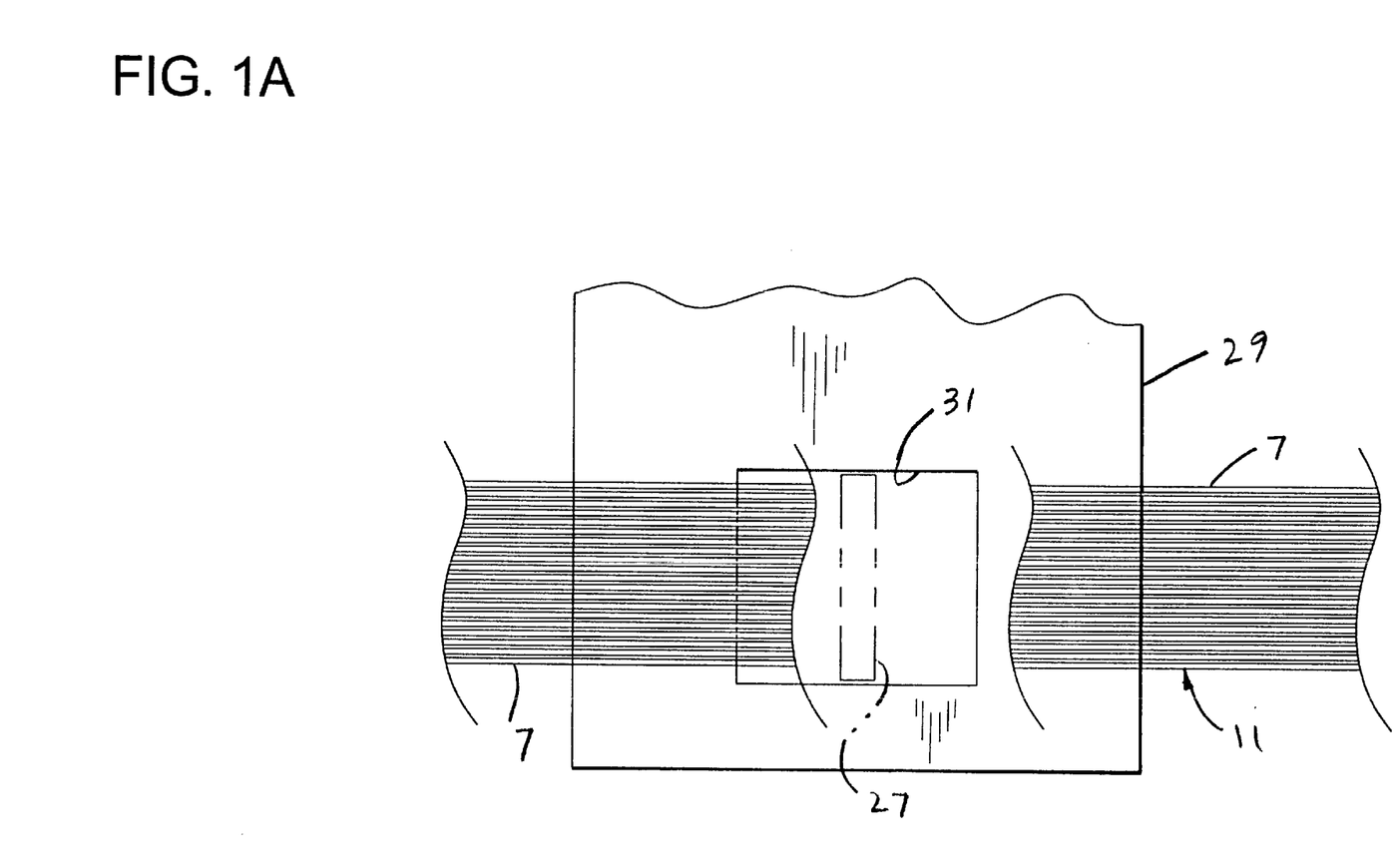
FIG. 1A is a plan view of a cooling body and an overlying array of capillary tubes.

Referring now to the drawings, FIG. 1 shows a multiplexed (parallel) capillary electrophoresis (CE) system, generally indicated at 1, for simultaneously separating and analyzing the components of multiple chemical samples. The system comprises a pair of hydrodynamic injectors of the present invention, the injector on the left as viewed in FIG. 1 being generally designated 3L and the injector on the right 3R. The system also includes a bundle 5 of capillary tubes 7 having left end portions (as viewed in FIG. 1) attached to the left injector 3L and right end portions attached to the right injector 3R. As will be explained in more detail later in this description, one or both of these injectors 3L, 3R can be used to substantially concurrently load samples to be analyzed into the capillary tubes 7 prior to the separation phase of an electrophoresis operation. The capillary tubes 7 have intermediate portions between the left and right end portions arranged in a generally planar, ribbon-like array 11 in which the intermediate portions extend side-by-side in closely spaced generally parallel relation (FIG. 1A). The array 11 lies in a horizontal plane as viewed in FIG. 1.

The system 1 also includes a power source 15 for applying a potential (voltage) difference between the ends of the capillary tubes 7 to cause an electrical current to flow through the contents of the tubes, a light source 19 for emitting light to pass through the closely spaced array 11 of intermediate portions of the capillary tubes, and a photodetector generally designated 21 comprising photodetector elements (not shown) for receiving light passing through the planar array 11 of intermediate portions of the capillary tubes. Light passing through the tubes is imaged on the photodetector 21 by an imaging lens, generally designated 25.

More specifically, the capillary bundle 5 may comprise a series of 96 capillary tubes 7, although this number may vary. For example, the capillary bundle 5 can include 8 or more capillaries, 16 or more, 24 or more, but more preferably 48 or more and most preferably 96 or more capillaries. Each tube is of relatively small diameter (e.g., 150 microns OD; 75 microns ID) and of a suitable electrically nonconductive material, such as fused silica so that high voltages can be applied across tube without generating excessive heat. The tubes 7 may have a polyimide coating which is removed by a laser beam, for example, in an area extending across the planar array of intermediate portions of the capillary tubes, thereby forming what may be referred to as a detection window (27 in FIG. 1A) which is transparent or translucent so that light from the light source can pass through the walls of the tubes at this location. Alternatively, the tubes 7 may be translucent or transparent along their entire lengths. The bundle 5 in the area adjacent the detection window 27 may be cooled by a suitable conductive cooling body 29 having a window 31 therein generally in alignment with the detection window. The cooling body 29 may be a thermoelectric device. Alternatively, the cooling body 29 may be cooled by coolant flowing through passages in the body, as described in copending application Ser. No. 09/621,890, filed Jul. 20, 2000; issued Apr. 8, 2003, as U.S. Pat. No. 6,544,396. The bundle 5 is of any appropriate length (e.g., 10 cm–2 m). As illustrated in FIG. 1, the bundle 3 may be supported by suitable supports 35 on opposite sides of the cooling body 29. The capillary tubes of the bundle may be held in the aforementioned planar array 11 by any suitable means, such as by strips of adhesive tape (not shown) extending across the array on opposite sides of the detection window 27.

The light source 19 may be of any suitable type, such as a deuterium or tungsten lamp or a 254-nm mercury lamp, emitting light having a certain wavelength (e.g., 200–800 nm and generalizable to other wavelengths) corresponding to the absorption band of the sample components of interest. The light is typically ultraviolet or visible light. Light emitted from the source 19 is adapted to pass through the detection window 27 and through the window of the cooling body 29 for incidence on the imaging lens 25 and photodetector 21 therebelow.

The photodetector 21 is of a conventional type, such as a photodiode device, having the aforementioned photodetector elements. These elements may be photodiodes, for example, arranged in one or more linear rows. For example, the photodetector may be a model C5964 multichannel detector head by Hamamatsu incorporating a linear image sensor chip, a low-noise driver/amplifier circuit, and a temperature controller. In this example, the linear image sensor chip has 1024 diodes, each of which is 25 microns in width and 2500 microns height. Other types of photodetectors can be used without departing from the scope of this invention. The photodetector elements generate output signals which are then transmitted to a digital processor 35 (FIG. 1) and related equipment (e.g., a computer 37) for generating and displaying an electropherogram 39, i.e., a plot of light intensity versus time, as will be understood by those skilled in this field. This plot can then be evaluated to identify components of interest in the samples being analyzed. As shown in FIG. 1, the electropherogram can be displayed on a screen 41 of the computer 37. Optionally, to improve the quality of the electropherogram, the photodetector 21 may be mounted for selective rotation about an axis generally perpendicular to the plane of the detection window 27, as described in copending U.S. patent application Ser. No. 09/621,890, filed Jul. 20, 2000; issued Apr. 8, 2003, as U.S. Pat. No. 6,544,396, incorporated herein by reference.

The imaging lens 25 may also be of conventional design, such as a quartz lens (Sodern f.1.=94 mm; F=4.1) in combination with an interference filter 45 (Oriel) employed to define the absorption wavelength. The lens 25 is positioned between the detection window 27 and the photodetector 25 to receive light passing through the capillary tubes 7 and to image that light on the linear array 11 of photodetector elements. The image of the capillary tubes 7 projected by the lens on the photodetector 25 may be an image 1.5 times actual size, for example.

Figure 2:
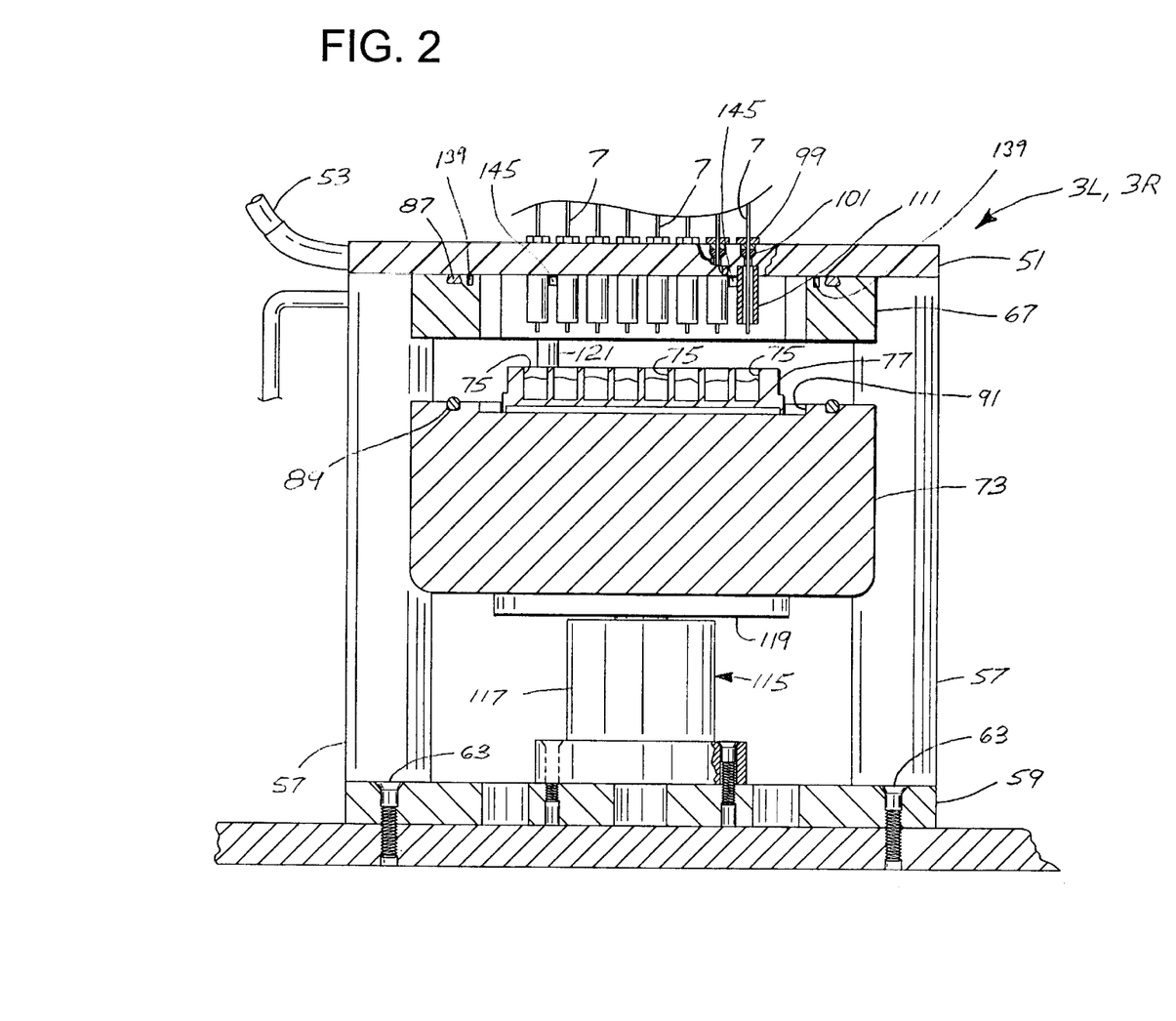
FIG. 2 is an enlarged vertical section on line 2—2 of FIG. 1 showing a hydrodynamic injector in an open position.
Figure 4:
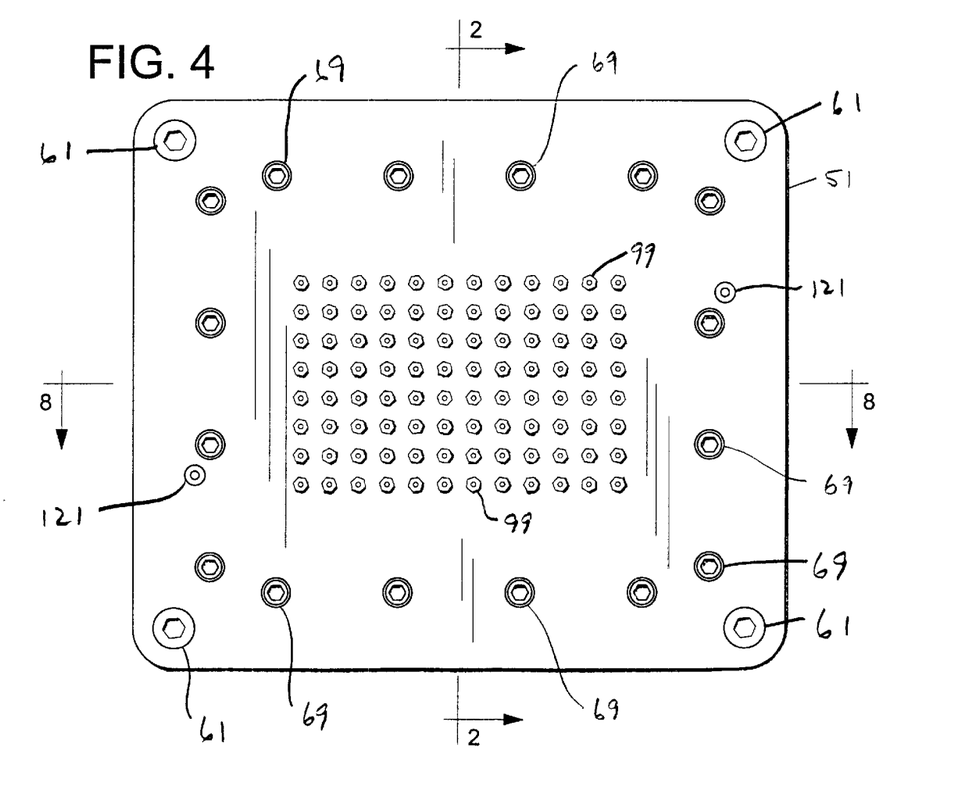
FIG. 4 is a plan view of a power plate of the injector.

The left and right injectors 3L, 3R are essentially identical in construction, so only one will be described. As shown in FIGS. 2 and 4, each injector 3L, 3R comprises a rectangular metal power plate 51 connected to the power source 15 by suitable electrical cable 53. The power plate may be of copper, for example. The power plate 51 is supported by four legs 57, one at each corner of the plate, having lower ends secured to a base plate 59. The legs are affixed to the power plate and base by fasteners 61 and 63, respectively. An annular sealing block 67 is fastened by suitable means (e.g., fasteners 69) to the underside of the power plate 51. The sealing block 67 is of a suitable dielectric material, such as Delrin® plastic. The injector 3 also includes a thick support block 73 of dielectric material (e.g., Delrin® plastic) for supporting a series of receptacles 75 containing samples to be analyzed. These receptacles may be the wells 75 of a standard 96-well microtiter plate 77, for example, although it will be understood that other receptacles may be used. The support block 73 is movable between a raised position (FIG. 2A) in which it is in sealing engagement with the sealing block 67 and a lowered (FIG. 2) position in which it is spaced from the sealing block. When the support block 73 is in its raised position, an enclosure (generally designated 81 in FIG. 2A) is formed defining a pressure chamber 83 receiving the microtiter plate 77 therein, the walls of the pressure chamber being formed by the bottom surface of the power plate 51, the interior walls of the annular sealing block 67, and the top surface of the support block 73. The pressure chamber 83 is sealed by an upper annular seal 87 between the power plate 51 and the sealing block 67 and by a lower annular seal 89 between the sealing block and the support block.

Figure 2A:
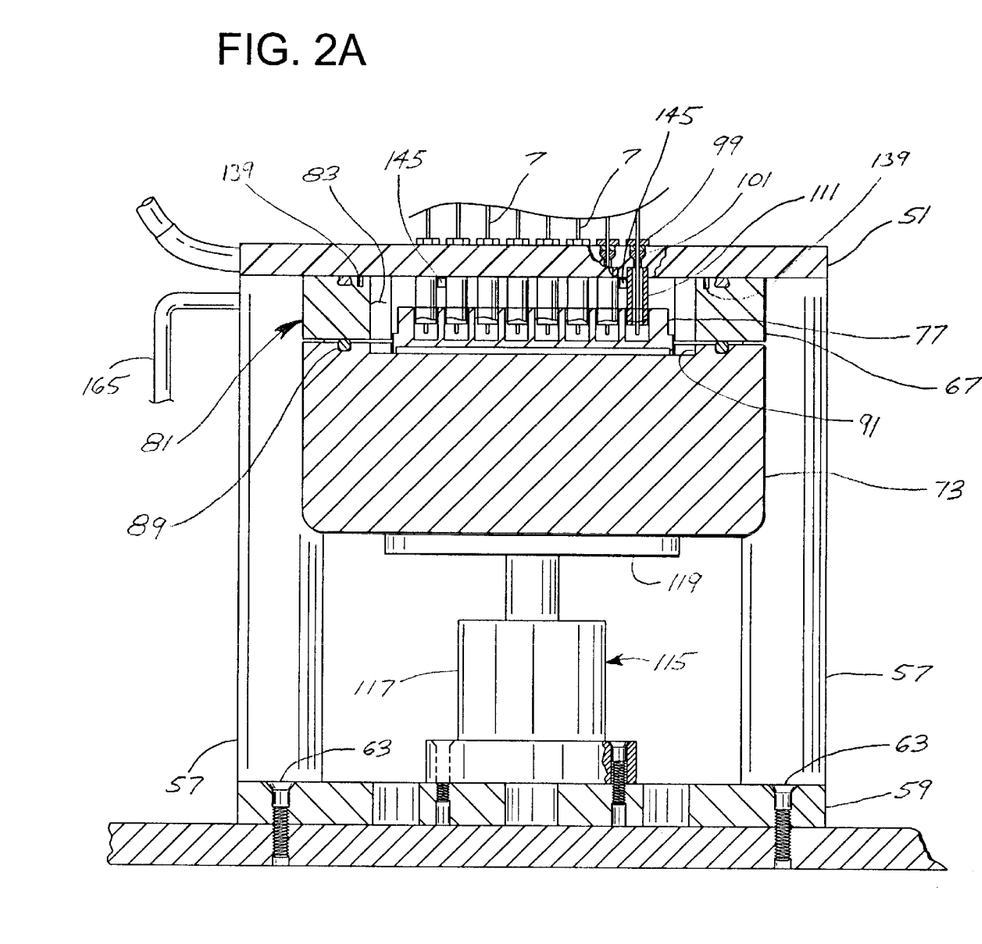
FIG. 2A is a view similar to FIG. 2 showing the injector in a closed position.
Figure 3:
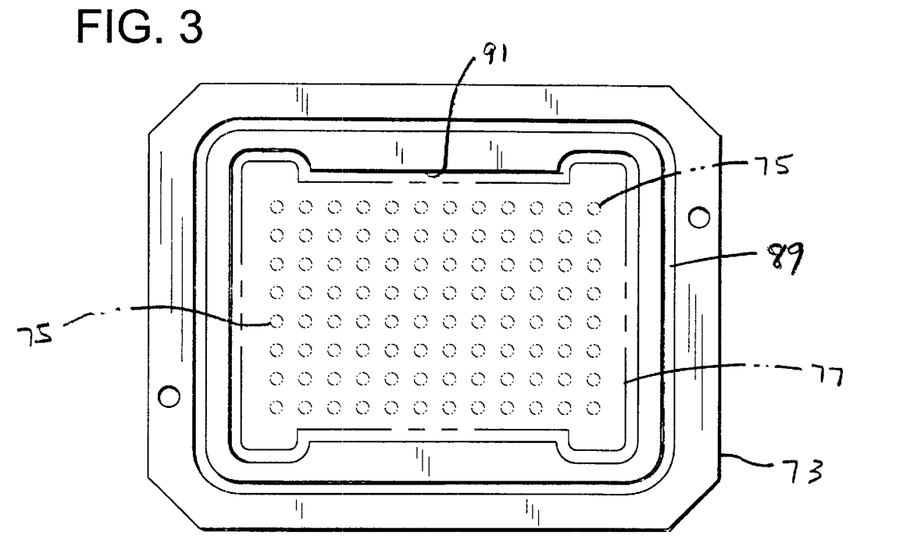
FIG. 3 is a plan view of a support block of the injector, a microtiter plate being shown in phantom positioned in a recess in the block.

As shown in FIGS. 2A and 3 the support block 73 has a recess 91 in its upper surface for holding the microtiter plate 77 or whatever other container is used for holding the samples. The outline of the recess 91 should be sized to hold the microtiter plate in a fixed predetermined position for reasons which will become apparent.

Figure 5:
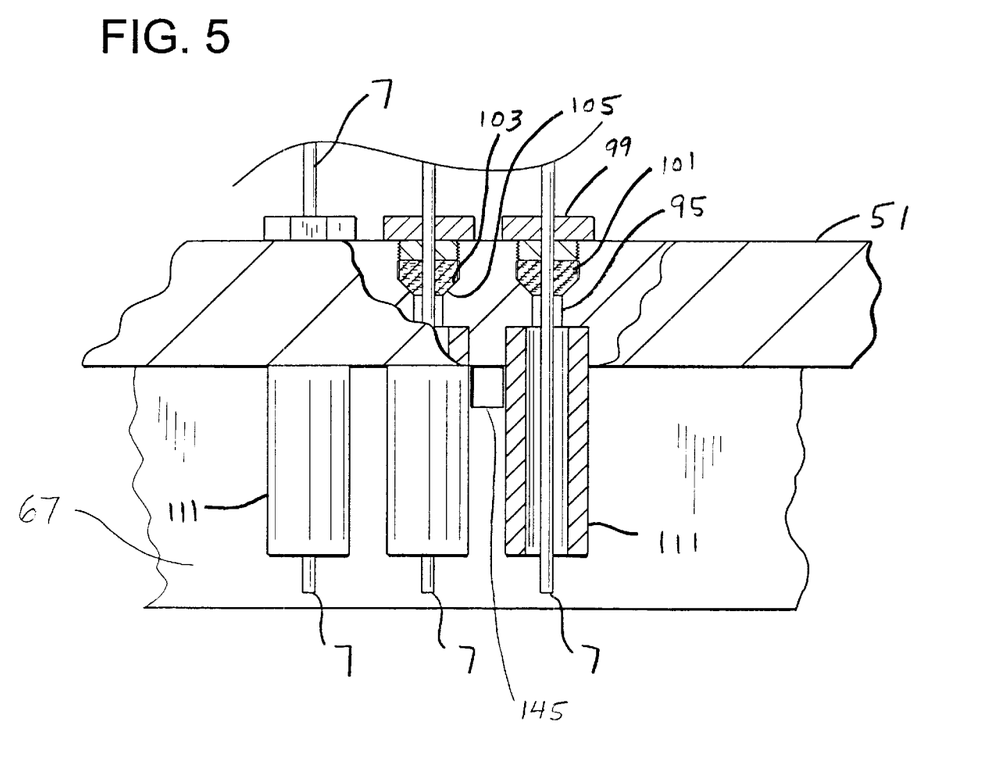
FIG. 5 is an enlarged fragmentary portion of FIG. 2 illustrating how the capillary tubes are affixed to the power plate.

Referring to FIG. 5, the power plate 51 has a series of vertical apertures 95 (holes) therein for passage of the capillary tubes 7 through the power plate to a position in which the tubes extend down from the plate for reception in respective wells 75 of the microtiter plate 77 when the support block 73 is in its raised position forming the aforementioned pressure chamber 83. Each capillary tube 7 is secured in position by a fitting comprising a stub screw 99 threaded in the upper end of a respective hole 95 and having an axial passage through it for receiving the tube 7, and a ferrule 101 in the hole 95 below the screw 99 having a conical surface 103 engageable with a tapered shoulder 105 in the hole. The design is such that threading the screw 99 down in the hole 95 against the ferrule 101 drives the conical surface 103 of the ferrule into sealing engagement against the tapered shoulder 105 of the hole and wedges the axial opening in the ferrule closed against the capillary tube 7 to clamp the tube securely in place without crushing or otherwise blocking the tube. The ferrule also forms a seal against the tube and power plate to prevent leakage through the hole 95. Other means may be used for sealingly securing the tube 7 in place without departing from the scope of this invention.

A series of tubular metal electrodes 111, one for each well 75 in the microtiter plate 77, are secured (e.g., brazed) to the lower face of the power plate 51 generally coaxially with the holes 95 in the plate for receiving the capillary tubes 7. Alternatively, the tubes 7 could extend down outside the electrodes 111. In either case, the electrodes 111 extend down from the plate 51 for reception in the wells 75, one electrode for each well, for electrifying the contents of the wells when the power source 15 is activated and when the support block 73 is in its raised position closing the pressure chamber 83. The power plate 51 and electrodes 111 are preferably of copper or other suitable metal and are preferably gold plated to render them chemically inert or non-reactive.

The support block 73 is movable up and down relative to the power plate by an actuator generally designated 115. The actuator may be a linear actuator such as a pneumatic cylinder 117 secured to the base 59 and having its rod end attached to a pusher plate 119 affixed to the support block 73. However, it will be understood that other types of power actuators or manually operated devices may also be used. The support block 73 is guided as it moves up and down by a pair of vertical guide pins 121 which extend down from the power plate 51 through edge grooves 123 (FIG. 6) in the periphery of the sealing block 67 for reception in clearance holes 125 in the support block (FIG. 8), each clearance hole having a diameter only slightly larger than that of the respective guide pin. The guide pins 121 are suitably affixed to the power plate 51, as by a press fit.

Figure 6:
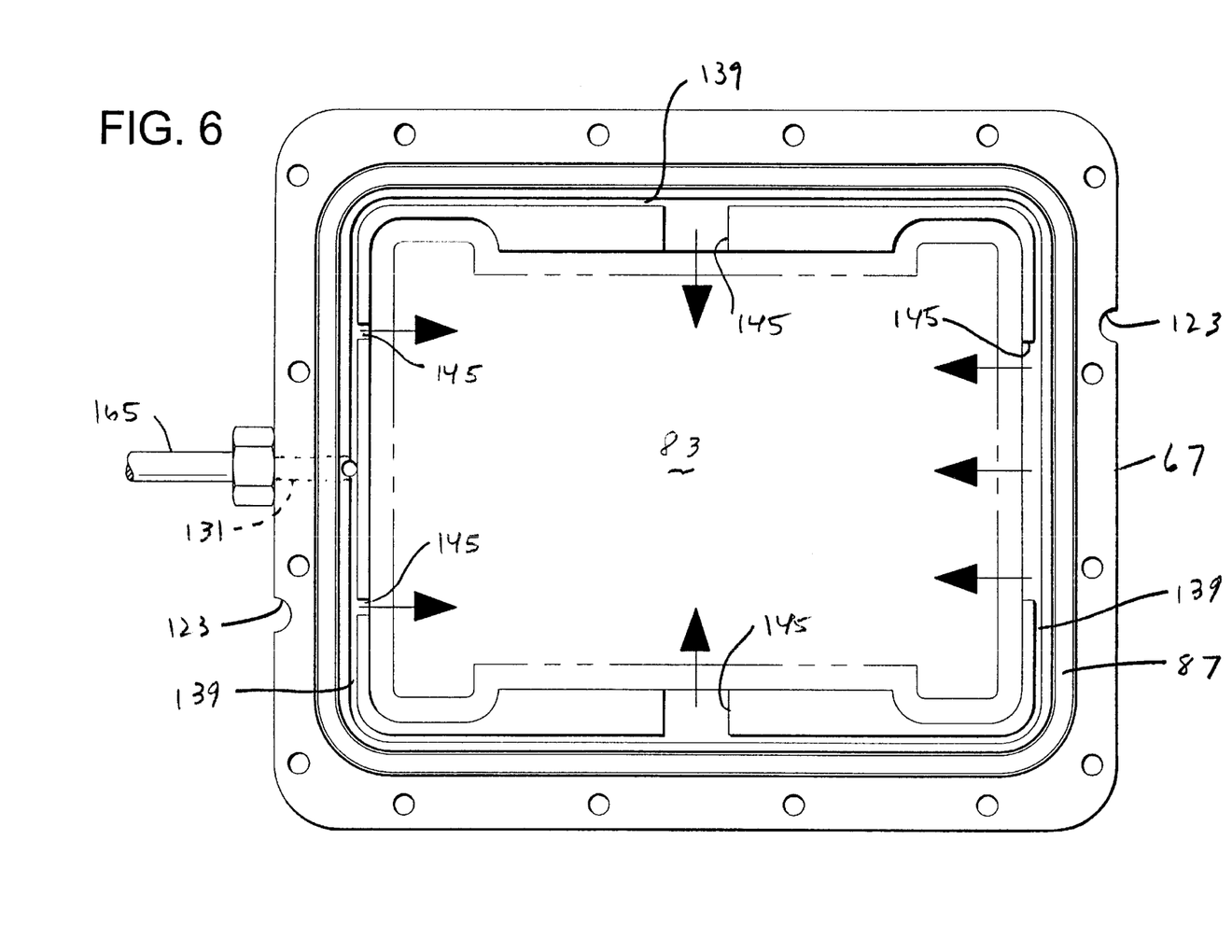
FIG. 6 is a bottom view of a sealing block of the injector, a microtiter plate being shown in phantom received inside an opening in the sealing block.
Figure 7:
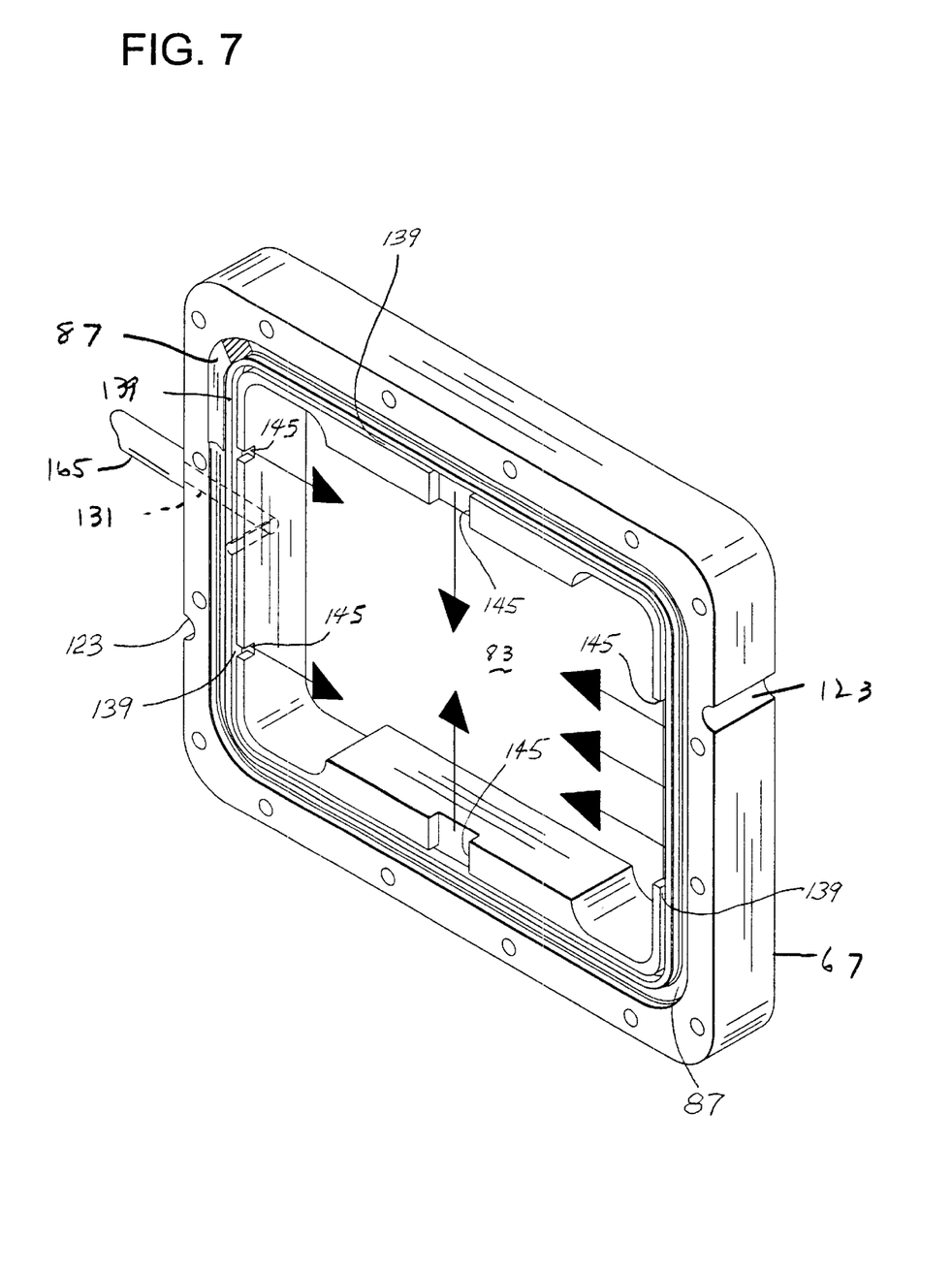
FIG. 7 is a perspective of the sealing block with portions of a seal being broken away to show details.
Figure 8:
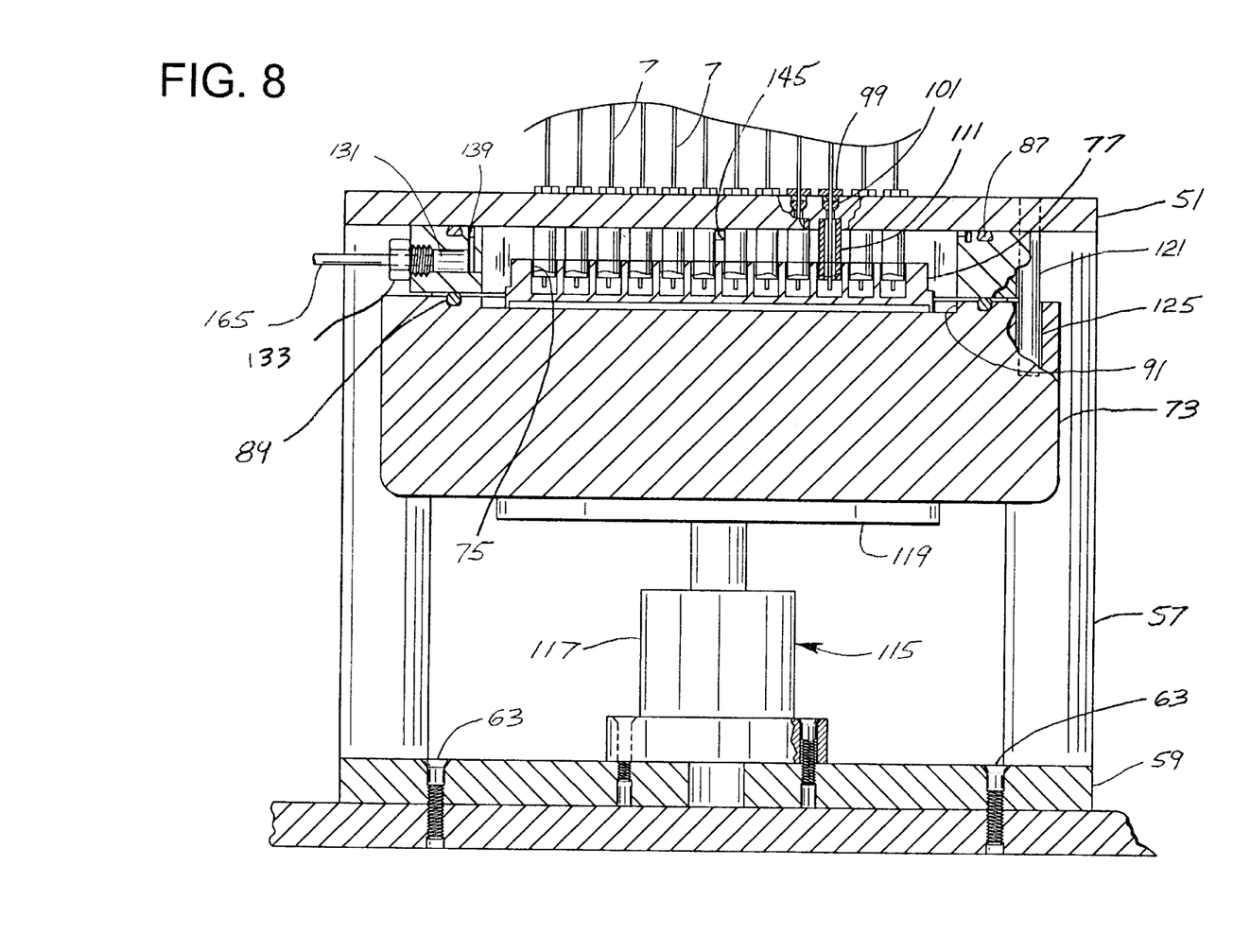
FIG. 8 is a section on line 8—8 of FIG. 4 showing the injector in a closed position.

As shown in FIGS. 6 and 8, the sealing block 67 has a generally horizontal bore 131 therein forming a gas inlet for the introduction of pressure gas into the pressure chamber 83 when the support block 73 is raised to form the aforementioned enclosure 81. The bore 131 has a fitting 133 at its upstream end for connection to a gas supply system, generally designated 135 in FIG. 1, for supplying gas under pressure to the pressure chamber 83. An annular channel 139 extending down from the upper face of the sealing block 67 surrounds the pressure chamber 83 and communicates with the inlet bore 131. The annular channel 139 communicates with the pressure chamber 83 via a plurality of passages formed, for example, by notches 145 in the upper face of the sealing block 67 spaced at intervals around the pressure chamber. Five such notches 145 are shown in FIG. 6, two relatively small notches closely adjacent the inlet 131 on opposite sides thereof at one side of the pressure chamber 83, a larger notch 145 on each of the two sides of the pressure chamber adjacent the side with the inlet, and a single very large notch 145 on the side of the pressure chamber opposite the inlet. This arrangement insures a uniform distribution of pressure air throughout the channel 139 for uniform and substantially instantaneous pressurization of the pressure chamber 83, as will be described in more detail later. The number of passages 145 and their configuration may vary.

The gas supply system 135 comprises a source of pressurized gas (e.g., cylinder 151), an accumulator 153 having an inlet 155 and an outlet 157, an accumulator inlet line 161 connecting the gas source 151 and the accumulator 153, and an accumulator outlet line 165 connecting the accumulator outlet and the inlet passage 131 in the sealing block 67. A conventional regulator 169 in the accumulator inlet line 161 reduces the pressure of the gas supplied from the cylinder 151 to an acceptable level (e.g., from about 2000 psi to about 40 psi). A pressure controller, generally designated 171, is also provided in the inlet line 161 for controlling the pressure in the accumulator. The pressure controller may be a closed-loop electronic control system including a proportioning control valve 175, PID (proportional, integrated and differential) control electronics 177 and a pressure transducer 179. The regulator 169 should reduce the pressure in line 161 to a level at or below the maximum input pressure of the pressure controller. The control system 171 may be purchased as an off-the-shelf integrated package, such as a 640 Series pressure controller commercially available from MKS Instruments, Inc. of Andover, Mass. Other pressure control systems may also be used, as will be understood by those skilled in this field. A shut-off valve 181 (e.g., a pneumatically driven shut-off valve) is provided in the accumulator outlet line 165. A valve suitable for this purpose is a diaphragm valve DA Series, Model 316L VAR, available from Nupro Company of Willoughby, Ohio.

The accumulator 153 is a hollow vessel of metal, for example, having a pressure chamber 185 therein, the volume of which is related to the volume of the pressure chamber 83 defined by the power plate 51, sealing block 67 and support block 73 when the latter is in its raised position. The ratio of the volume of this latter chamber 83 to the accumulator chamber 185 is in the range of about 5:1—about 1:5, more preferably in the range of about 2:1—about 1:2, and most preferably about 1:1. The accumulator 153 may be of two-part construction, comprising upper and lower parts capable of being releasably secured together in sealing relation. The precise construction is not important to the present invention. A vent line 187 is connected to the accumulator 153 for venting the interior of the accumulator. The vent line 187 includes a fine leak valve 191 and a shutoff valve 193. The shut-off valve 193 may be a valve identical to the shut-off valve 181 in the accumulator outlet line 165. A suitable fine leak valve 191 is a BM Series bellows sealed metering valve available from Nupro Company of Willoughby, Ohio.

As noted previously, the CE system shown in FIG. 1 includes two injectors 3L, 3R for receiving opposite ends of the capillary tubes 7 of the bundle 5. The left ends of the tubes of the bundle extend down into the pressure chamber 83 defined by the power plate 51, sealing block 67 and support block 73 of the left injector 3L, and the right ends of the tubes extend down into the pressure chamber 83 defined by the power plate 51, sealing block 67 and support block 73 of the right injector 3R. However, as will be described later, the present invention can be practiced using only one injector at either end of the bundle of capillary tubes.

The bundle 5 of capillary tubes, injectors 3L, 3R, light source 19, cooling body 29, imaging lens 25 and photodetector 21 are preferably enclosed in a thermally insulated enclosure 201 having one or more doors 203. One or more convective coolers 207 are provided in the enclosure 201 for cooling it and maintaining the interior of the enclosure at a desired temperature.

In use, the CE system 1 of the present invention may be set up as shown in FIG. 1, where the array 11 of the intermediate portions of the parallel capillary tubes 7 drape over the two supports 35 and rest flat on the cooling body 29 in a position in which the detection window 27 of the tubes is in registry with the window 31 in the cooling body so that light from the light source 19 will pass through the detection window and the window in the cooling body for incidence on the imaging lens 25 and photodetector 21.

After the capillary tubes 7 are flushed and loaded with a suitable buffer solution ("conditioned"), samples to be analyzed are loaded into the tubes in accordance with the present invention. Assuming the samples are to be loaded into the right ends of the capillary tubes as shown in FIG. 1, a microtiter plate 77 (or other multi-receptacle container) carrying the samples to be analyzed is placed in the recess 91 in the top surface of the support block 73 of the right injector 3R when the support block 73 is in its lowered position. The cylinder 117 is then actuated to move the block 73 to its raised position in which the support block is sealed against the sealing block 67 to form the stated pressure chamber 83 containing the samples. In this position, the right ends of the capillary tubes extend down into the wells 75 of the microtiter plate 77 and contact the samples. The electrodes 111 on the power plate 51 also extend down into the wells and contact the samples. (The microtiter plate is positioned by the recess 91 to insure proper alignment between the electrodes 111 and wells 75.) A second microtiter plate 77 (or other container) is placed in the recess 91 in the upper surface of the support block 73 of the left injector 3L, below the left ends of the capillary tubes, for receiving waste from the tubes. The support block 73 of the second injector 3L can either be maintained in its lowered position or moved to its raised position during the loading process.

Loading of samples into the right ends of the capillary tubes is effected by introducing gas under pressure into the pressure chamber 83 of the right injector 3R. This process is initiated by closing the shut-off valve 181 in the accumulator outlet line 165 and the valves 191, 193 in the accumulator vent line 187, and by opening the proportioning valve 175 to permit entry of pressurized gas into the accumulator chamber 185 until the pressure in the accumulator reaches a predetermined pressure P1, as indicated by the pressure transducer 179. The shut-off valve 181 in the accumulator outlet line is then opened, which permits gas to enter the pressure chamber 83 via inlet passage 131, channel 139 and notches 145. The pressure in the chamber 83 should rapidly reach equilibrium at the desired injection pressure P2, which is preferably about 1–100 millibars, more preferably about 10–40 millibars and most preferably about 20 millibars, preferably in less than about one second. It will be noted in this regard that if the gaseous volume of the pressure chamber 83 is V1, the initial pressure in the chamber 83 is P0 (e.g., ambient), and the gaseous volume of the accumulator chamber 185 is V2, then the final injection pressure P2, under ideal gas laws, can be determined to be: $P2=P0(V1/(V1+V2))+P1(V2/(V1+V2))$. Assuming the desired injection pressure P2 is 20 millibars, for example, and the ratio of V1 to V2 is 1:1, then the accumulator pressure P1 should be 40 millibars before the shut-off valve is opened; if the ratio of V1 to V2 is 5:1, then P1 should be 120 millibars; if the ratio is 1:5, then P1 should be 24 millibars. (It will be noted in this regard that volumes V1 and V2 are "gaseous" volumes, meaning the volume of space occupied by gas. Therefore, when the chamber 83 holds a microtiter plate 77, V1 is the volume of the chamber 83 when unoccupied less the volume of space occupied by the plate 77 and samples therein. The volume V2 of the accumulator chamber 185 is the volume of the unoccupied chamber. The volume of the accumulator chamber may vary, with one suitable volume being three cubic inches.)

Upon pressurization of the pressure chamber 83, the samples in the wells 75 of the microtiter plate 77 are forced substantially concurrently into the right ends of the capillary tubes 7. This is allowed to continue for a predetermined amount of time (e.g., ten seconds) sufficient to inject a plug of sample into each tube, following which the proportioning valve 175 is closed and the vent valves 191, 193 are opened to vent the accumulator 153 and the pressure chamber 83 to atmosphere.

Following sample loading, and prior to the start of an electrophoresis operation, the cooling system is actuated to cool the interior space of a thermally insulated system enclosure 201 enclosing the two injectors 3L, 3R and the capillary tubes therein. This involves actuating the one or more convective cooling units 207 and also the conduction cooling device 29 for a time sufficient to bring the interior air temperature of the enclosure down to a temperature sufficient to prevent overheating of the capillary tubes and the contents thereof, which is particularly important during a chiral separation process involving the generation of substantial heat. A temperature in the range of about 0–99° C., preferably in the range of about 0–40° C. and most preferably about 20° C., is believed to be suitable for this purpose.

After the enclosure 201 and capillary tubes 7 are suitably cooled, the power source 15 is activated to apply a voltage to the tubes 7, causing the various components of the samples to migrate at different speeds to effect separation, as will be understood by those skilled in this field. To separate chiral molecules, a relatively large current is required (e.g., a sum total of 1–20 milliamps for a bundle of 96 capillary tubes), which results in the generation of a substantial amount of heat in the tubes and contents thereof. The conduction heat transfer device 29 removes this heat in the area of the bundle generally adjacent the detection window 27, where the capillary tubes 7 are relatively closely spaced. The convective heat transfer units 207 remove this heat from other portions of the bundle 5. As a result, overheating of the capillary tubes 7 and contents thereof is prevented, thus ensuring a more accurate analysis of the samples.

Light from the light source 19 passes through the planar array 11 of the capillary tubes 7 and is projected by the lens 25 as an image of the tubes onto the photodiodes of the photodetector 21. These diodes generate signals which are processed in conventional fashion to generate and display an electropherogram 39 plotting light intensity (indicative of absorption levels) versus time.

As the electrophoresis operation proceeds, sample solution flows through the capillary tubes 7 and into one or more receptacles 75 on the support block 73 of the left injector 3L. A 96-well microtiter plate 77 may be used if there is a need or desire to maintain the collected solution in each tube separate from the solutions in the other tubes, as when different buffer solutions are used in different tubes during the same test run.

Optionally, a second electrophoresis operation may be carried out by pressurizing the left pressure chamber of the left injector 3L to a pressure greater than the pressure in the pressure chamber of the right injector 3R to force fluid from the receptacles in the pressure chamber of 3L into the second ends of the capillary tubes, and thereafter causing an electric current to flow through the capillary tubes and contents thereof to cause capillary electrophoresis during which fluid flows from the pressure chamber of injector 3L to the first pressure chamber of injector 3R.

It will be apparent from the foregoing that samples can be loaded into either end of the bundle 5 and that sample flow through the tubes can be in either direction. Also, the position of the detection window 27 can be varied relative to the injectors so that DI in FIG. 1 is not equal to D2. In other words, the detection window 27 can be positioned at a location other than midway between the two injectors 3L, 3R. As a result, two different capillary "separation lengths" are achieved using the same bundle. ("Separation length" is the distance between the sample loading end of the bundle and the detection window 27.) The provision of two different separation lengths may be useful, since different types of samples may require different separation lengths, and since a shorter separation length may be sufficient for sample analysis not requiring precise results.

As noted previously, the capillary tubes 7 are "conditioned" (i.e., flushed and filled with buffer solution) prior to each run. Conditioning is readily accomplished using the setup shown in FIG. 1. A container containing a suitable cleaning solution is simply placed on the support block 73 of the right injector 3R, for example, and the block is then moved to its raised position in which the pressure chamber 83 is closed and the ends of the capillary tubes are received in the container. The accumulator is then pressurized, leaving the shut-off valve 181 in the accumulator outlet line 165 open, so that cleaning solution is forced through the capillary tubes and collected in a suitable waste receptacle on the support block of the other (e.g., left) injector 3L. The procedure is repeated to fill the tubes with buffer solution.

A CE operation can be carried out using only one injector at one end of the bundle, instead of two injectors. If only one injector is used at one end of the bundle, the opposite end of the bundle should be placed in an electrically grounded receptacle containing buffer solution prior to the beginning of a run.

It will be understood that the construction of the injector 3L, 3R may vary without departing from the scope of this invention. For example, while the pressure chamber 83 is described as being formed by the power plate 51, sealing block 67 and support block 73, the chamber may be formed by other parts of other configurations, any one of which parts may be movable to provide access to the interior of the chamber for placement of one or more sample receptacles therein. Similarly, the accumulator 153 of the gas supply system 135 can take many forms. It is important, however, that the accumulator 153 be sized relative to the pressure chamber 83 so that pressure equilibrium is reached very quickly after the shut-off valve 181 in the accumulator outlet line 165 is opened.

For additional detail regarding the cooling system 29, 207, reference may be made to copending U.S. patent application Ser. No. 09/621,890, filed Jul. 20, 2000; issued Apr. 8, 2003, as U.S. Pat. No. 6,544,396, incorporated herein by reference.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A hydrodynamic injector for simultaneously loading fluid samples to be analyzed into multiple capillary tubes of a capillary electrophoresis system, said tubes having first and second ends, said injector comprising:

an enclosure defining a pressure chamber for holding multiple receptacles, each containing a fluid sample therein, apertures in the enclosure for passing capillary tubes into a position wherein first ends of the tubes are positioned in said pressure chamber in fluid communication with the samples in respective receptacles, electrodes on the enclosure extending into the pressure chamber for reception in said receptacles; and a pressurization system comprising a gas supply system for supplying pressurized gas to said pressure chamber, said gas supply system comprising a source of pressurized gas, an accumulator having an inlet and an outlet, an accumulator inlet line connecting the source of pressurized gas to the inlet of the accumulator, an accumulator outlet line connecting the accumulator to a gas inlet of the enclosure, and a valve in the accumulator outlet line movable from a closed position to an open position after the accumulator has been pressurized for effecting the transfer of gas under pressure from the accumulator to the pressure chamber of the enclosure.

2. An injector as set forth in claim 1 wherein said enclosure includes a movable part movable between an open position away from the enclosure to permit access to said receptacles and a closed position in sealing relation with the enclosure so that the pressure chamber can be pressurized.

3. An injector as set forth in claim 2 wherein said movable part is configured for supporting a tray having said multiple receptacles therein.

4. An injector as set forth in claim 3 further comprising a power actuator for moving said moveable part between said open and closed positions.

5. An injector as set forth in claim 4 wherein said movable part has a surface with a recess therein sized and shaped to receive said tray and to hold it in a fixed predetermined position relative to said movable part.

6. An injector as set forth in claim 1 further comprising means for fixedly and sealingly securing the capillary tubes in respective apertures in the enclosure.

7. An injector as set forth in claim 1 further comprising a pressure controller in said accumulator inlet line for controlling the pressure in said accumulator.

8. An injector as set forth in claim 7 wherein said pressure chamber has a first volume and said accumulator has a second volume, the ratio of said first volume to said second volume being in the range of 5:1–1:5.

9. An injector as set forth in claim 8 wherein said ratio is in the range of 2:1–1:2.

10. An injector as set forth in claim 9 wherein said ratio is about 1:1.

11. An injector as set forth in claim 1 wherein said accumulator outlet line and the gas inlet of the enclosure are sized so that pressure equilibrium in said pressure chamber is reached at about one second after said valve is opened.

12. An injector as set forth in claim 1 further comprising a vent system for venting the accumulator and said pressure chamber when said valve is open.

13. An injector system as set forth in claim 1 wherein said enclosure is a first enclosure and said system further comprises a second enclosure having a second chamber therein containing one or more receptacles for receiving fluid samples transmitted through the capillary tubes from the first enclosure, apertures in the second enclosure for passing said capillary tubes into a position wherein second ends of the tubes are positioned in said second chamber for the flow of fluid into said one or more receptacles, and electrodes on the second enclosure extending into the second chamber for reception in said one or more receptacles.

14. An injector as set forth in claim 1 further comprising a system for cooling said pressure chamber to cool the first ends of said capillary tubes.

15. A method as set forth in claim 14 wherein a least some of said samples contain chiral molecules, and wherein said electric current is sufficient to effect separation of said chiral molecules.

16. A hydrodynamic injector system for simultaneously loading fluid samples to be analyzed into multiple capillary tubes of a capillary electrophoresis system, said tubes having first and second ends, said injector system comprising:

a first injector comprising a first enclosure defining a first pressure chamber for holding multiple receptacles, each containing a fluid sample therein, apertures in the first enclosure for passing capillary tubes into a position wherein first ends of the tubes are positioned in said first pressure chamber in fluid communication with the samples in respective receptacles, electrodes on the first enclosure extending into the first pressure chamber for reception in said receptacles;

said first enclosure having a gas inlet for pressurizing the first pressure chamber whereby said fluid samples are simultaneously forced from respective receptacles into the first ends of respective capillary tubes in preparation for a capillary electrophoresis operation, a second injector comprising a second enclosure having a second pressure chamber therein containing one or more receptacles for receiving fluid samples transmitted through the capillary tubes from the first enclosure, apertures in the second enclosure for passing said capillary tubes into a position wherein second ends of the tubes are positioned in said second pressure chamber for the flow of fluid into said one or more receptacles, and electrodes on the second enclosure extending into the second pressure chamber for reception in said one or more receptacles, said second pressure chamber being adapted for holding multiple receptacles, each containing a fluid sample therein, said second enclosure having a gas inlet for pressurizing the pressure chamber whereby said fluid samples in the second enclosure are simultaneously forced from respective receptacles into the second ends of respective capillary tubes in preparation for a capillary electrophoresis operation, and a thermally insulated system enclosure defining an interior space enclosing said capillary tubes and said first and second injectors, including said first and second pressure chambers, and a cooling system for cooling said interior space of said system enclosure, said first and second injectors, and said capillary tubes.

17. An injector system as set forth in claim 16 wherein said capillary tubes extend between said first and second enclosures and have portions defining a detection window for the passage of light therethrough, said detection window being at a location closer to one enclosure than the other.

18. An injector system as set forth in claim 16 wherein said cooling system comprises one or more convective cooling units for cooling said interior space of said system enclosure, and a conduction cooling device for cooling said capillary tubes.

19. A method of capillary electrophoresis involving the simultaneous transfer of fluid samples from multiple receptacles into first ends of multiple capillary tubes, said method comprising:

positioning the first ends of the capillary tubes and the receptacles in a single pressure chamber so that the first ends are in fluid communication with the samples in the receptacles, pressurizing the pressure chamber by pressurizing an accumulator to a predetermined pressure and, after said predetermined pressure has been reached, opening a valve to establish gas flow communication between the accumulator and said pressure chamber to pressurize the pressure chamber, and causing an electric current to flow through the capillary tubes and contents thereof to cause a first capillary electrophoresis operation.

20. A method as set forth in claim 19 wherein said pressurizing step is carried out so that the pressure in said pressure chamber reaches equilibrium in no longer than about one second after said gas flow communication is established.

21. A method as set forth in claim 20 further comprising sizing the volumes of the pressure chamber and accumulator so that the ratio of the pressure chamber volume to said accumulator volume is in the range of 5:1–1:5.

22. A method as set forth in claim 21 wherein said ratio is in the range of 2:1–1:2.

23. A method as set forth in claim 22 wherein said ratio is about 1:1.

24. A method as set forth in claim 19 further comprising cooling the pressure chamber to cool the first ends of said capillary tubes.

25. A method as set forth in claim 19 wherein a least some of said samples contain chiral molecules, and wherein said electric current is sufficient to effect separation of said chiral molecules.

26. A method of capillary electrophoresis involving the simultaneous transfer of fluid samples from multiple receptacles into first ends of multiple capillary tubes, said method comprising:
    positioning the first ends of the capillary tubes and the receptacles in a single first pressure chamber so that the first ends are in fluid communication with the samples in the receptacles,
    pressurizing the first pressure chamber to force fluid from the receptacles into the capillary tubes,
    causing an electric current to flow through the capillary tubes and contents thereof to cause a first capillary electrophoresis operation,
    positioning second ends of the capillary tubes in a second pressure chamber containing multiple receptacles for receiving said second ends, and
    cooling the capillary tubes, said cooling comprising cooling an interior space defined by a thermally insulated system enclosure enclosing said first and second pressure chambers and said capillary tubes.

27. A method as set forth in claim 26 further comprising causing a second electrophoresis operation by pressurizing the second pressure chamber to a pressure greater than the pressure in said first pressure chamber to force fluid from the receptacles in the second pressure chamber into the second ends of the capillary tubes, and causing an electric current to flow through the capillary tubes and contents thereof to cause capillary electrophoresis during which said fluid flows from the second pressure chamber to said first pressure chamber.

28. A method as set forth in claim 26 further comprising detecting the flow of said fluid samples as they move through the capillary tubes at a location other than midway between said first and second pressure chambers.

29. A method as set forth in claim 26 wherein said cooling further comprises cooling portions of said capillary tubes by conduction cooling.

30. A hydrodynamic injector for simultaneously loading fluid samples to be analyzed into multiple capillary tubes of a capillary electrophoresis system, said tubes having first and second ends, said injector comprising:
    an enclosure defining a pressure chamber for holding multiple receptacles, each containing a fluid sample therein,
    apertures in the enclosure for passing capillary tubes into a position wherein first ends of the tubes are positioned in said pressure chamber in fluid communication with the samples in respective receptacles;
    electrodes on the enclosure extending into the pressure chamber for reception in said receptacles;
    said enclosure having a gas inlet for pressurizing the pressure chamber whereby said fluid samples are simultaneously forced from respective receptacles into the first ends of respective capillary tubes in preparation for a capillary electrophoresis operation; and
    a channel in said enclosure surrounding the pressure chamber and communicating with said gas inlet, and passages connecting the channel and the pressure chamber at spaced intervals around the pressure chamber.

31. A method of capillary electrophoresis involving the simultaneous transfer of fluid samples from multiple receptacles into first ends of multiple capillary tubes, said method comprising:
    positioning the first ends of the capillary tubes and the receptacles in a single pressure chamber so that the first ends are in fluid communication with the samples in the receptacles,
    pressurizing the pressure chamber to force fluid from the receptacles into the capillary tubes, and
    causing an electric current to flow through the capillary tubes and contents thereof to cause a first capillary electrophoresis operation,
    said pressurizing step comprising pressurizing an accumulator to a predetermined pressure and, after said predetermined pressure has been reached, opening a valve to establish gas flow communication between the accumulator and said pressure chamber to pressurize the pressure chamber.

32. A hydrodynamic injector system for simultaneously loading fluid samples to be analyzed into multiple capillary tubes of a capillary electrophoresis system, said tubes having first and second ends, said injector system comprising:
    a first injector comprising an first enclosure defining a first pressure chamber for holding multiple receptacles, each containing a fluid sample therein, apertures in the first enclosure for passing capillary tubes into a position wherein first ends of the tubes are positioned in said first pressure chamber in fluid communication with the samples in respective receptacles, and electrodes on the first enclosure extending into the first pressure chamber for reception in said receptacles;
    said first pressure chamber being adapted for pressurization whereby said fluid samples are simultaneously forced from respective receptacles into the first ends of respective capillary tubes in preparation for a capillary electrophoresis operation;
    a second injector comprising a second enclosure having a second pressure chamber therein containing one or more receptacles for receiving fluid samples transmitted through the capillary tubes from the first enclosure, apertures in the second enclosure for passing said capillary tubes into a position wherein second ends of the tubes are positioned in said second pressure chamber for the flow of fluid into said one or more receptacles, and electrodes on the second enclosure extending into the second pressure chamber for reception in said one or more receptacles;
    said second pressure chamber being adapted for holding multiple receptacles, each containing a fluid sample therein, and being adapted for pressurization whereby said fluid samples in the second enclosure are simultaneously forced from respective receptacles into the second ends of respective capillary tubes in preparation for a capillary electrophoresis operation;
    a thermally insulated system enclosure defining an interior space enclosing said first and second injectors, including the first and second pressure chambers, and said capillary tubes; and
    a cooling system for cooling said interior space of said system enclosure, said first and second injectors, and said capillary tubes.

33. A system as set forth in claim 32 wherein said cooling system comprises one or more convective cooling units for cooling said interior space of said system enclosure, and a conduction cooling device for cooling said capillary tubes.

* * * * *